(12) United States Patent
Watanabe et al.

(10) Patent No.: US 9,662,007 B2
(45) Date of Patent: May 30, 2017

(54) OPHTHALMOLOGIC APPARATUS

(71) Applicant: CANON KABUSHIKI KAISHA, Tokyo (JP)

(72) Inventors: Kazuhiro Watanabe, Tokyo (JP); Hidero Matsumoto, Nishitokyo (JP); Tetsuya Sekine, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 123 days.

(21) Appl. No.: 14/596,518

(22) Filed: Jan. 14, 2015

(65) Prior Publication Data

US 2015/0208913 A1 Jul. 30, 2015

(30) Foreign Application Priority Data

Jan. 28, 2014 (JP) ................................. 2014-013588

(51) Int. Cl.
*A61B 3/00* (2006.01)
*A61B 3/14* (2006.01)
*A61B 3/15* (2006.01)

(52) U.S. Cl.
CPC ............ *A61B 3/0083* (2013.01); *A61B 3/005* (2013.01); *A61B 3/0075* (2013.01); *A61B 3/152* (2013.01)

(58) Field of Classification Search
CPC ..... A61B 3/0083; A61B 3/005; A61B 3/0075; A61B 3/152
USPC ........................................................ 351/206
See application file for complete search history.

(56) References Cited

U.S. PATENT DOCUMENTS

| 8,857,993 | B2 * | 10/2014 | Nakajima | A61B 3/0075 351/245 |
| 8,939,965 | B2 * | 1/2015 | Liesfeld | A61B 3/0033 351/206 |
| 2009/0195750 | A1 * | 8/2009 | Isogai | A61B 3/0075 351/208 |
| 2011/0260882 | A1 * | 10/2011 | Lee | H04M 1/72577 340/686.6 |
| 2013/0278898 | A1 * | 10/2013 | Kato | A61B 3/1005 351/208 |

(Continued)

FOREIGN PATENT DOCUMENTS

| JP | 2011-245028 A | 12/2011 |
| JP | 2012-45083 A | 3/2012 |

*Primary Examiner* — Bumsuk Won
*Assistant Examiner* — Grant Gagnon
(74) *Attorney, Agent, or Firm* — Carter, DeLuca, Farrell & Schmidt, LLP

(57) ABSTRACT

Provided is an ophthalmologic apparatus, which is configured to perform observation and photographing of an eye to be examined via an objective lens, and which allows the observation or the like of the eye to be examined irrespective of a posture of an examinee. The ophthalmologic apparatus includes: a main body part including an optical system and the objective lens that are configured to perform the observation and the photographing; a stand part configured to support the main body part with respect to an installation surface; a chin rest part configured to place a chin of an examinee thereon; and a forehead rest configured to bring a forehead of the examinee into abutment therewith. In the ophthalmologic apparatus, the chin rest part, the forehead rest, and the objective lens can be integrally changed in elevation angle with respect to the stand part.

10 Claims, 6 Drawing Sheets

(56) References Cited

U.S. PATENT DOCUMENTS

| | | | |
|---|---|---|---|
| 2013/0286348 A1* | 10/2013 | Makihira | A61B 3/1025 351/206 |
| 2014/0218688 A1* | 8/2014 | Verdooner | A61B 3/102 351/208 |
| 2015/0265144 A1* | 9/2015 | Burlina | A61B 3/10 351/206 |
| 2015/0282702 A1* | 10/2015 | Koennecke | A61B 3/0083 351/245 |
| 2015/0335234 A1* | 11/2015 | Okada | A61B 3/0083 351/208 |

* cited by examiner

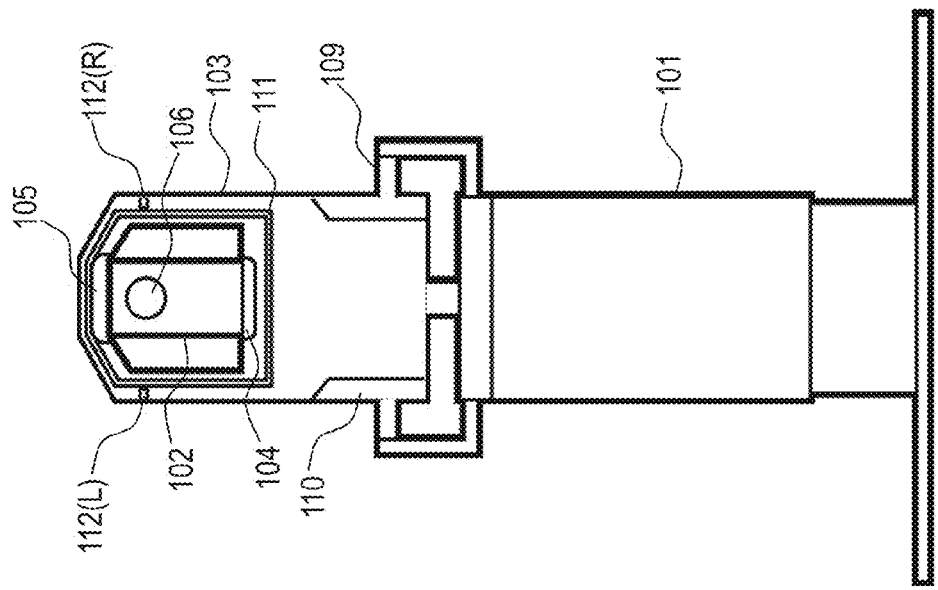
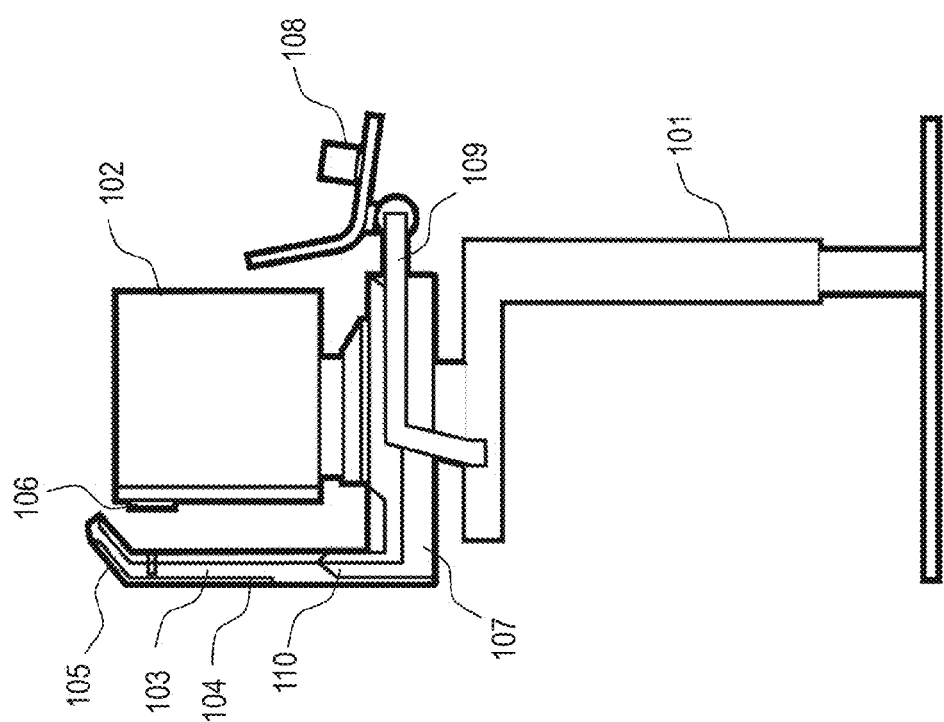

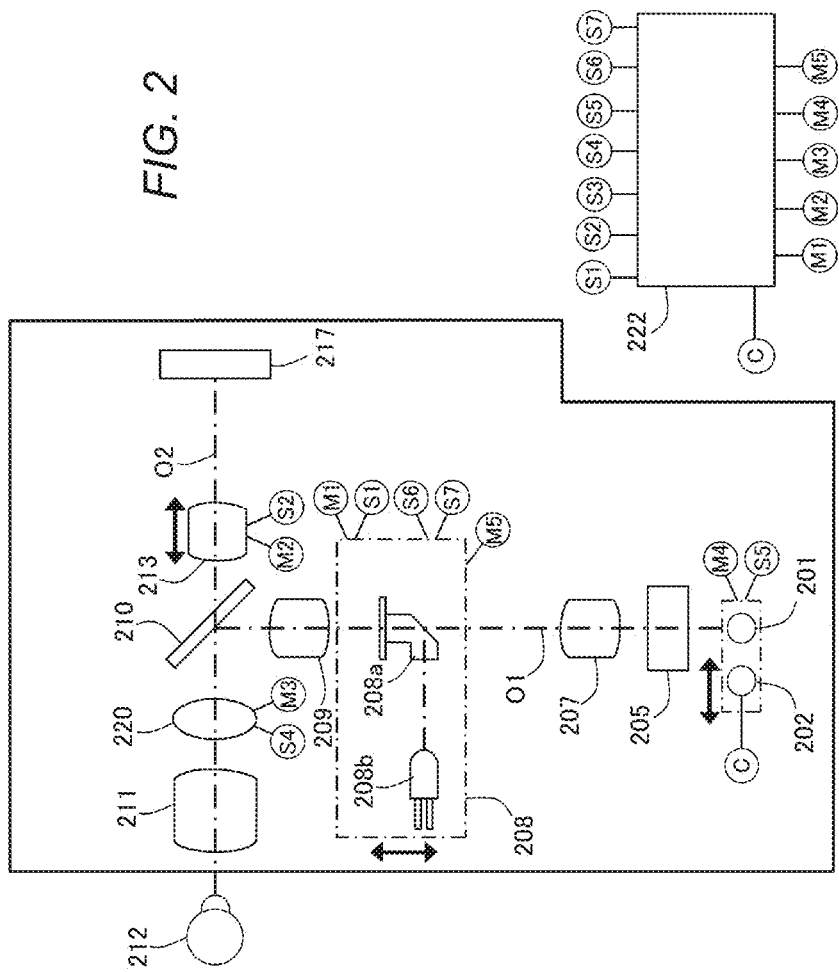

OPHTHALMOLOGIC APPARATUS

BACKGROUND OF THE INVENTION

Field of the Invention

The present invention relates to an ophthalmologic apparatus configured to execute an examination of an eye to be examined through observation or photographing thereof.

Description of the Related Art

An ophthalmologic apparatus configured to observe or photograph an eye to be examined is generally supported by a stand for installing an apparatus main body on a flat surface such as a floor or a desk. The ophthalmologic apparatus includes components such as a so-called rack, a camera main body part serving as the apparatus main body, a chin rest part, and a forehead rest, and those components are arranged in order on this stand.

The rack supports the camera main body part so as to be able to slide in a substantially horizontal direction (front-back/left-right direction) relative to the above-mentioned flat surface. Further, the camera main body part stores various optical systems and control systems. The chin rest part is used to place a chin of an examinee at a time of an examination. The forehead rest is used to bring a forehead of the examinee into abutment therewith. The optical system of the camera main body part includes an objective lens located so as to be opposed to the eye to be examined and an image pickup lens configured to form an image of the eye to be examined on an image pickup element. Further, the ophthalmologic apparatus is electrically connected to the camera main body part, and also includes an operation part configured to allow an examiner to perform instructions/operations of image pickup and the like.

The camera main body part is demanded to perform, at a time of the examination, alignment between an optical system for the eye to be examined and the eye to be examined or a change of a range for observation or photographing of the eye to be examined. Therefore, the camera main body part can change in angle toward the eye to be examined in regard to up-down and left-right directions on the rack. Note that, in general, the change in angle in the up-down direction is referred to as "elevation", and the change in angle in the left-right direction is referred to as "swing".

Japanese Patent Application Laid-Open No. 2012-45083 discloses an ophthalmologic image pickup apparatus configured to allow the elevation and the swing of the camera main body part with respect to the eye to be examined. Specifically, an elevation unit and a swing unit are arranged in the ophthalmologic image pickup apparatus.

The swing unit supports a photographing unit so as to oscillate in a substantially horizontal direction about a substantially vertical first axis, the first axis being substantially in contact with an anterior ocular segment of the eye to be examined. Further, the elevation unit supports the photographing unit so as to oscillate in a substantially up-down direction about a substantially horizontal second axis, the second axis being substantially in contact with the anterior ocular segment of the eye to be examined. A monitor unit configured to present the photographed image is mounted to the swing unit, and is further configured to oscillate integrally with the photographing unit about the first axis.

Further, Japanese Patent Application Laid-Open No. 2011-245028 discloses an ophthalmologic image pickup apparatus provided with a tilt mechanism for elevating a photographing part in the up-down direction relative to the eye to be examined. The ophthalmologic apparatus can perform an action of the elevation by the tilt mechanism formed of a guide member, a moving member, a coupling member, and the like. The guide member has an arc shape formed about a given point on a photographing optical axis of an image pickup optical system extending toward the eye to be examined. The moving member is rotatably mounted to the apparatus main body, and is moved along the guide member. The coupling member couples a rotation shaft formed to the guide member to the moving member, and is rotationally driven by a drive part. The moving member is moved relative to the rotation shaft by the rotation of the coupling member, which causes the apparatus main body to tilt in the up-down direction along the guide member.

Related-art ophthalmologic image pickup apparatus including the ophthalmologic image pickup apparatus disclosed above are based on an assumption that the examinee undergoes an examination with his/her face fixed temporarily perpendicularly. However, the examinee includes a person, for example, a weak-kneed elderly person, whose face is hardly fixed substantially perpendicularly. With the above-mentioned ophthalmologic image pickup apparatus, it is difficult to execute an examination (observation or photographing) for such an examinee due to the arrangement of the chin rest part, the forehead rest, and the like provided based on the above-mentioned assumption.

SUMMARY OF THE INVENTION

The present invention has been made in order to solve such a problem, and an object thereof is to provide an ophthalmologic apparatus with which an examination is easy to carry out even for an examinee whose face is hardly fixed substantially perpendicularly.

According to one embodiment of the present invention, there is provided an ophthalmologic apparatus, which is configured to perform observation and photographing of an eye to be examined via an objective lens. The ophthalmologic apparatus including: a main body part including an optical system and the objective lens that are configured to perform the observation and the photographing; a stand part configured to support the main body part with respect to an installation surface; a chin rest part configured to place a chin of an examinee thereon; and a forehead rest configured to bring a forehead of the examinee into abutment therewith, in which the chin rest part, the forehead rest, and the objective lens are configured to be integrally changed in elevation angle with respect to the stand part.

According to one embodiment of the present invention, it is possible to provide the ophthalmologic apparatus with which an examination is easy to carry out even for an examinee such as a bent elderly person whose face is hardly fixed substantially perpendicularly.

Further features of the present invention will become apparent from the following description of exemplary embodiments with reference to the attached drawings.

BRIEF DESCRIPTION OF THE DRAWINGS

FIG. 1A is a side view illustrating a configuration example of an ophthalmologic apparatus according to a first embodiment of the present invention, and FIG. 1B is a front view thereof.

FIG. 2 is a block diagram illustrating a configuration example of a camera main body part illustrated in FIGS. 1A and 1B.

DESCRIPTION OF THE EMBODIMENTS

Figure 3A:
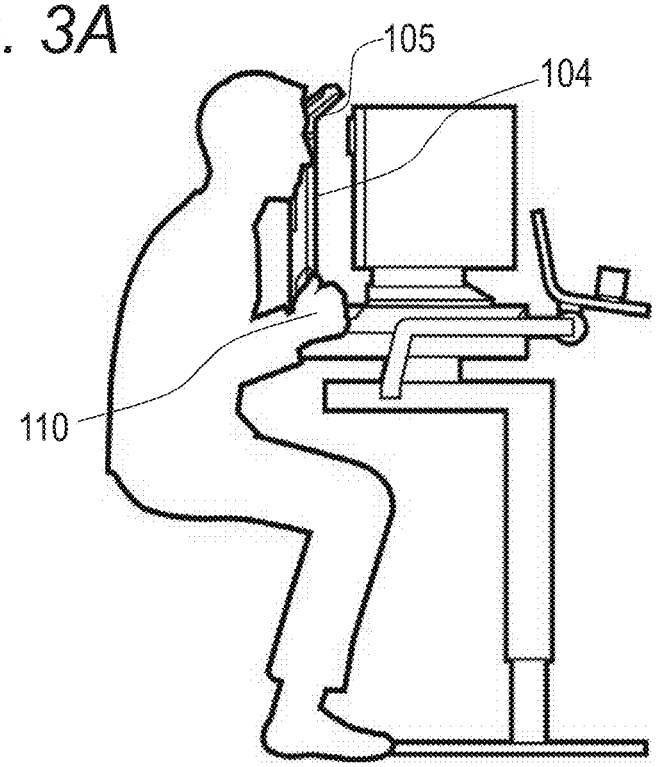
FIGS. 3A and 3B are views each illustrating a use mode of the ophthalmologic apparatus according to the first embodiment of the present invention.

Preferred embodiments of the present invention will now be described in detail in accordance with the accompanying drawings.

(First Embodiment)

A schematic configuration of an ophthalmologic apparatus according to a first embodiment of the present invention is described with reference to FIGS. 1A and 1B.

FIG. 1A is a side view illustrating a configuration example of the ophthalmologic apparatus according to this embodiment, and FIG. 1B is a front view thereof.

In FIGS. 1A and 1B, the ophthalmologic apparatus includes a stand part 101, a camera main body part 102, a frame part 103, an eyepiece part 106, a rack part 107, an operation panel 108, a guide rail part 109, and a grip handle part 110. The stand part 101 supports an ophthalmologic apparatus main body with respect to an installation surface formed of a flat surface such as a floor or a desk, and is installed on the installation surface. The camera main body part 102 corresponds to the main body part, and includes the eyepiece part 106, an optical system illustrated in FIG. 2 including a lens unit and an image pickup part, and a control part. The frame part 103 includes a chin rest part 104 for placing the chin of an examinee and a forehead rest 105 for bringing the forehead into abutment therewith. The rack part 107 couples the camera main body part 102 and the frame part 103 to the stand part 101.

The operation panel 108 includes an operation member (not shown) such as a joystick and a display part (not shown). The operation member is operated to thereby allow the operation of at least one operation portion within the camera main body part 102. Further, the display part displays an observed image or a photographed image of an eye to be examined. The guide rail part 109 guides the operation panel 108 so as to be able to move around the rack part 107. Note that, it is preferred that the guide rail part 109 be placed so as to be located around the camera main body part 102 while the installation surface is parallel with a predetermined plane on which the camera main body part 102 is slidably supported. The grip handle part 110 is grasped by the examinee at the time of an examination or the like to be used to maintain his/her posture for the examination.

Further, the ophthalmologic apparatus includes a light-emitting part 111 configured to accompany the frame part 103 and to inform the examinee of the position of the frame part 103 by emitting light. Further, in the same manner, cameras 112R and 112L for positional adjustment for determining a positional relationship between the examinee and the frame part 103 by photographing the examinee are located in the frame part 103.

The frame part 103 (including chin rest part 104 and forehead rest 105) and the camera main body part 102 (including eyepiece part 106, lens unit, image pickup part, and control part) are allowed by the rack part 107 to integrally change the elevation angle with respect to the stand part 101. Note that, it is preferred that the elevation angle as used herein be defined as an angle formed between the optical axis of the eyepiece part 106 and the installation surface or the predetermined plane described later. Further, the camera main body part 102 (including eyepiece part 106) can move in up-down/left-right directions relative to the frame part 103 independently of the change in the elevation angle, and is supported so as to be able to slide within the predetermined plane with respect to the rack part 107.

The camera main body part 102 is moved relative to the frame part 103 to perform alignment between the eye to be examined and an optical system for the eye to be examined included in the camera main body part 102, or to change an observation/photographing range of the eye to be examined. In contrast, the change in the elevation angle performed for the frame part 103 and the camera main body part 102 integrally with respect to the stand part 101 serves to freely set an angle used when the examinee temporarily fixes his/her face by the chin rest part 104 and the forehead rest 105.

FIG. 2 is a block diagram illustrating a configuration example of the camera main body part 102 of the ophthalmologic apparatus according to this embodiment.

An infrared LED light source 201 is a light source used when a fundus of the examinee is subjected to infrared observation. A light source 202 is a white LED light source or a visible light source, and is a light source used when the fundus of the examinee is subjected to photographing using visible light.

An infrared ring slit 205 is a mask for shaping illumination light from the infrared LED light source 201 into ring illumination. A capacitor C supplies power to the white LED light source 202. An amount of electric charge accumulated in the capacitor C differs depending on a photographing mode, and appropriate charge/discharge is performed each time the photographing mode is changed. The charge/discharge is controlled by a system control part 222.

The system control part 222 performs driving control for a drive part M1 to a drive part M5 described later, control of a sensing part S1 to a sensing part S7, control based on an input from a user interface (not shown), and control such as image data processing or displaying processing of the photographed image onto the display part. The white LED light source 202 and the infrared LED light source 201 are removably inserted onto an illumination optical path O1 by the drive part M4. On the illumination optical path O1, the infrared LED light source 201 is inserted at the time of the observation. After a photograph button (not shown) of the operation panel is pressed down to send out a trigger signal to the system control part 222, the infrared LED light source 201 is switched over to the white LED light source 202. After that, the white LED light source 202 is again switched over to the infrared LED light source 201. The white LED light source 202 and the infrared LED light source 201 are turned off when it is determined by the system control part 222 that the observation has not been performed for a predetermined time period. The ring illumination is imaged on an eye to be examined 212 by an illumination relay lens 207 and an illumination relay lens 209.

A split unit 208 includes a focus indicator 208a, a light source 208b, the drive parts M1 and M5, and the sensing parts S1, S6, and S7. The light source 208b is used as a light source for projecting an image of the focus indicator 208a. The split unit 208 is located in the illumination optical path 01 at the time of the observation, and the drive part M1 moves the split unit 208 in a direction indicated by the arrow in FIG. 2, to thereby function as a split driving motor configured to move the focus indicator 208a along an optical axis direction. That is, the drive part M1 drives the split unit 208 to achieve alignment with a focus position of a focus indicator, and the sensing part S1 detects a stop location of the split unit 208 or the focus indicator 208a as a split position sensing part. Further, the drive part M5 drives the split unit 208 in a direction different from the direction indicated by the arrow in FIG. 2, and performs insertion/removal of the split unit 208 to/from the illumination optical path O1. The sensing part S6 and the sensing part S7 both function as a position sensing part for the split unit 208, and detect the stop location of the split unit 208 when the driving thereof is stopped by the drive part M5.

A holed mirror 210 is a total reflection mirror having a hole at a center thereof, and is configured to cause the above-mentioned ring illumination to be reflected by the circumferential mirror to reach the eye to be examined and to cause photographing light from the eye to be examined to pass through the hole at the center. The ring illumination reflected by the holed mirror 210 is applied to the eye to be examined 212 so as to be imaged on the eye to be examined 212 by an objective lens 211. The reflected light from the eye to be examined 212 is imaged at the center of the holed mirror 210 after passing through the objective lens 211. A photographing optical axis 02 is an optical axis reaching an image pickup element 217 from the fundus of the examinee.

When an anterior ocular observation lens 220 is inserted into the photographing optical axis O2, it is possible to observe an anterior eye. On the other hand, when the anterior ocular observation lens 220 is not inserted into the photographing optical axis O2, it is possible to observe the fundus. The insertion/removal of the anterior ocular observation lens 220 to/from the photographing optical axis O2 is performed by using the drive part M3 serving as an anterior ocular observation lens driving motor and the sensing part S4 serving as an anterior ocular observation lens position sensing part. When the trigger signal, which is issued by pressing an anterior ocular alignment switching button (not shown) of the operation panel, is sent out to the system control part 222, the system control part 222 executes switching control for the insertion/removal of the anterior ocular observation lens 220.

The image pickup element 217 photo-electrically converts the photographing light. An electric signal that has been photo-electrically converted is converted into digital data by the system control part 222. The observed image is displayed on the display part at a time of the infrared observation, and at a time of the photographing, the photographed image is displayed on the display part and recorded on a recording medium (not shown) within the system control part 222. A focus lens 213 is a lens for performing focus adjustment for photographing luminous flux having passed through the hole at the center of the holed mirror 210, and is caused to move in the direction indicated by the arrow of FIG. 2 to thereby perform the focus adjustment. The drive part M2 serving as a focus lens driving motor drives the focus lens 213 by a pulse received from the system control part 222. The sensing part S2 serving as the position sensing part detects the position of the driven focus lens 213.

Figure 3B:
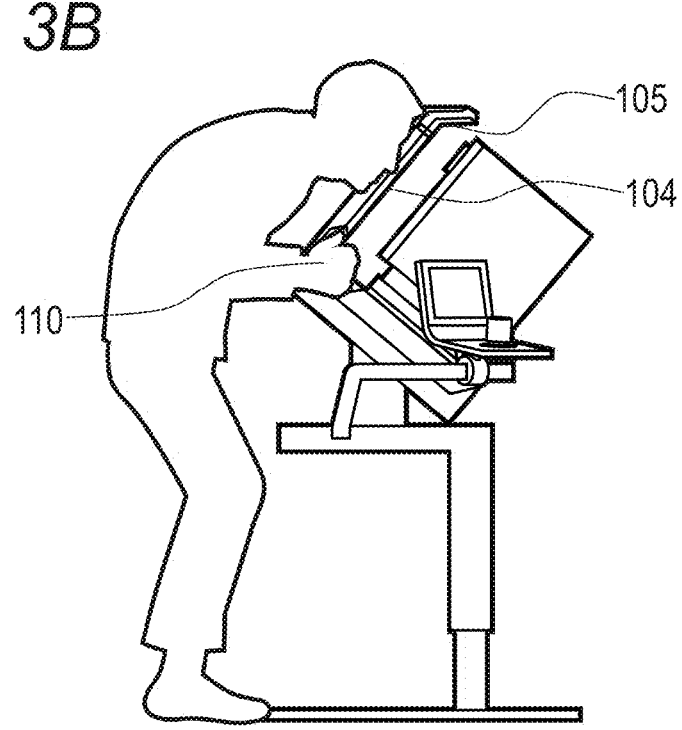

FIGS. 3A and 3B are views each illustrating a use mode of the ophthalmologic apparatus according to the first embodiment of the present invention.

In FIG. 3A, the frame part 103 including the chin rest part 104 and the forehead rest 105 are substantially perpendicular to the installation surface, and the examinee fixes his/her face substantially perpendicularly by the chin rest part 104 and the forehead rest 105.

In FIG. 3B, integrally with the camera main body part 102, the frame part 103 changes the elevation angle with respect to the stand part 101 so that a plane opposed to the face of the examinee or the optical axis of the eyepiece part 106 is directed upward.

In other words, the examinee can fix his/her face at such an angle as to bend his/her head by the chin rest part 104 and the forehead rest 105.

By thus allowing the change in the elevation angle, it becomes easy to undergo an ophthalmologic examination even for an examinee such as, for example, a bent elderly person whose face is hardly fixed substantially perpendicularly. Further, at this time, the grip handle part 110 is changed in the elevation angle integrally with the frame part 103 or the like, and hence the examinee can support his/her posture by grasping the grip handle part 110, which further facilitates the undergoing of the examination while maintaining the posture.

In this embodiment, the stand part 101 is stretchable so as to be able to adjust a height of the apparatus main body from the installation surface. Further, the stand part 101 is configured to form a space opened on an examinee side vertically below the camera main body part 102 or the rack part 107 so as to reserve a space for receiving a knee part of the examinee on the examinee side as illustrated in FIG. 1A, FIG. 3A, or FIG. 3B. Therefore, by adjusting the height of the apparatus in addition to the above-mentioned change in the elevation angle, it is possible to fix the face with a preferred posture even for each of examinees different in physical constitution. This also realizes the ophthalmologic apparatus that facilitates the undergoing of the examination even for the examinee whose face is hardly fixed substantially perpendicularly.

Note that, the camera main body part 102 can be moved in up-down and left-right directions relative to the frame part 103 in order to change the observation/photographing range of the eye to be examined, and this movement is independent of the above-mentioned change in the elevation angle performed integrally with the frame part 103. In other words, the observation/photographing range of the eye to be examined or the alignment therewith is not changed even when the elevation angle is integrally changed for the camera main body part 102 and the frame part 103 after the observation/photographing range of the eye to be examined is changed or the alignment with the eye to be examined is performed.

Further, the position/angle of the operation panel 108 does not follow the integral change in the elevation angle of the frame part 103 and the camera main body part 102, which does not change an operating posture of the operator (examiner).

In other words, according to the first embodiment of the present invention, the ophthalmologic apparatus configured to perform the observation and the photographing of the eye to be examined via the eyepiece part 106, in particular, an objective lens, is provided with the camera main body part 102 including the optical system and the objective lens for performing the observation and the photographing, the stand part 101 configured to support the camera main body part 102 with respect to the installation surface, the chin rest part 104, and the forehead rest 105. Further, the elevation angle can be changed for the chin rest part 104, the forehead rest 105, and the objective lens integrally relative to the stand part 101. With the above-mentioned configuration, it is possible to carry out an examination with ease even for the examinee such as a bent elderly person whose face is hardly fixed substantially perpendicularly without requesting an impossible posture. Further, with the configuration provided with the grip handle part 110, it is preferred that the grip handle part 110 be changed in the elevation angle integrally with the eyepiece part 106 or the like. When the examinee grasps the grip handle part 110 at the time of the examination, it becomes easy to maintain an examination posture, and it is possible to present a more preferred examination environment.

(Second Embodiment)

As a second embodiment of the present invention, an example of an ophthalmologic apparatus including the guide rail part 109 located around the rack part 107 with the operation panel 108 mounted to the guide rail part 109 slidably and rotatably is described.

Figure 4A:
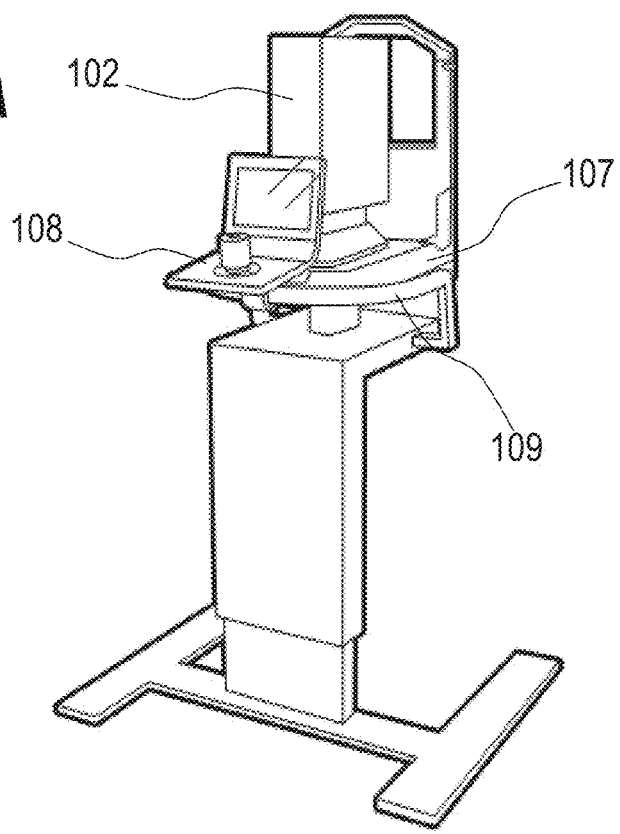
FIGS. 4A and 4B are perspective views each illustrating a configuration example of the ophthalmologic apparatus according to the first embodiment of the present invention.

FIG. 4A is a perspective view from an operator (examiner) side of the ophthalmologic apparatus according to this embodiment.

In FIG. 4A, the operation panel 108 is mounted onto the guide rail part 109 in substantially the same direction as an optical axial direction of the lens unit of the camera main body part 102. The operation panel 108 is further electrically connected to the camera main body part 102 and the rack part 107 through a cable or in a wireless manner. The operator (examiner) performs instructions/operations for the sliding of the camera main body part 102 in a front-back/left-right direction and the change in the elevation angle of the rack part 107 by the operation member such as a joystick located on the operation panel 108.

Figure 4B:
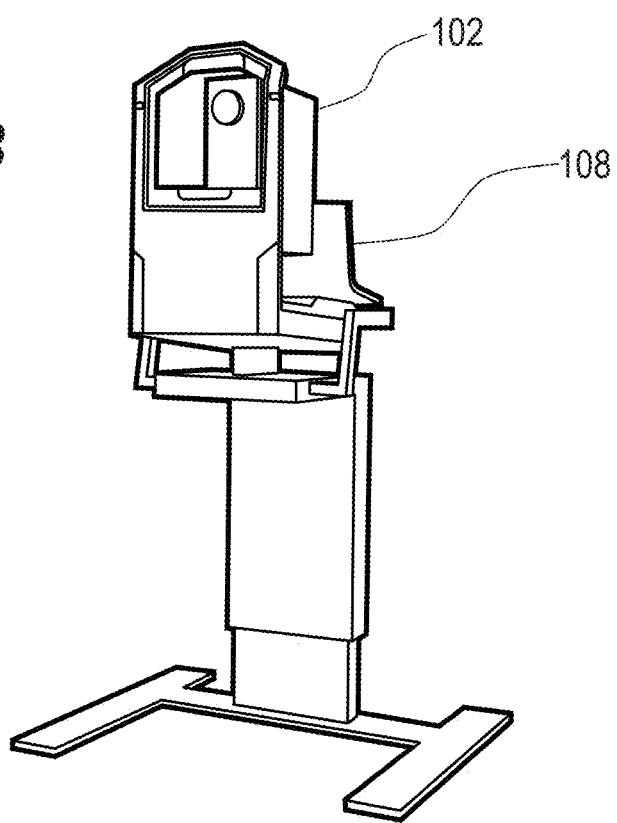

FIG. 4B is a perspective view from an examinee side of the ophthalmologic apparatus according to this embodiment.

As illustrated in FIGS. 4A and 4B, in a state in which the direction of the operation panel 108 is substantially the same as the optical axial direction of the camera main body part 102, the operator (examiner) easily achieves alignment between an operation direction of the operation member and a movable direction of the apparatus (camera main body part 102), which facilitates the operation. However, it is desired that the operation panel 108 can be changed in position so as to approach the examinee when the examinee is to be provided with some assistance, for example, when his/her hand is to be put so as to prevent an eyelid of the examinee from covering the eye to be examined.

Figure 5A:
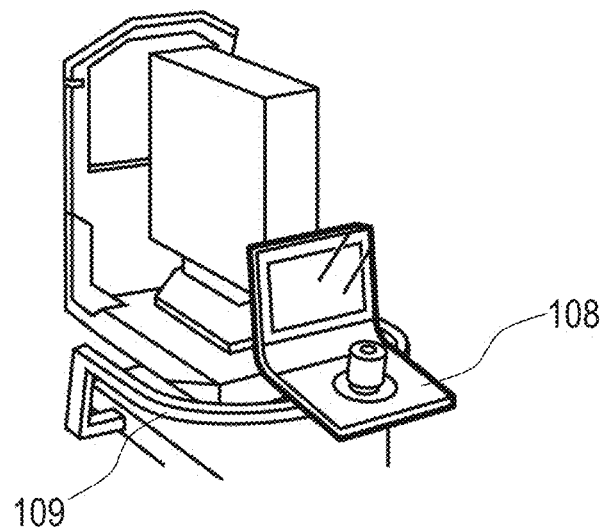
FIGS. 5A, 5B, and 5C are views each illustrating a use mode of an ophthalmologic apparatus according to a second embodiment of the present invention.
Figure 5B:
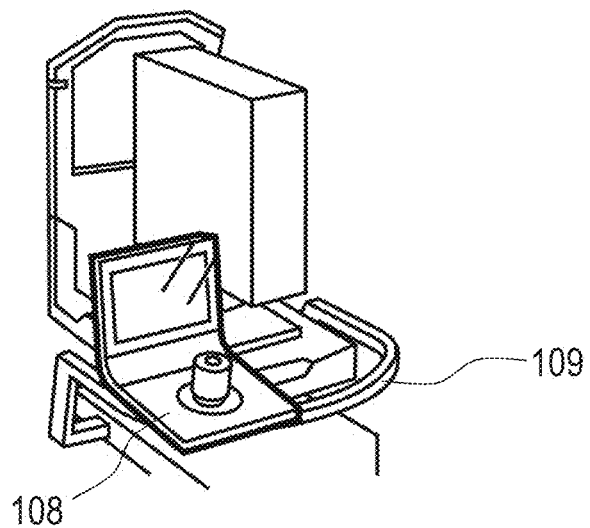
Figure 5C:
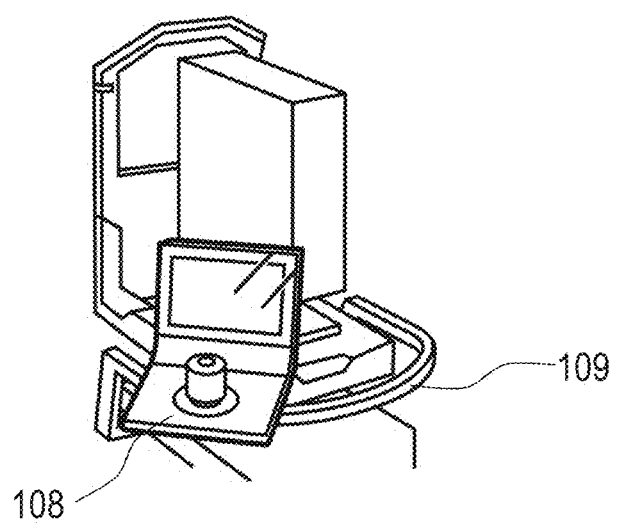

FIGS. 5A to 5C are views each illustrating a use mode of the ophthalmologic apparatus according to this embodiment.

FIG. 5B indicates a state in which the operation panel 108 is moved to slide on the guide rail part 109 while maintaining the same orientation as an orientation illustrated in FIG. 5A. In this state, a distance from the examinee becomes shorter, which facilitates the assistance for the examinee.

FIG. 5C indicates a state in which the operation panel 108 is rotated so that the display part is directed toward the operator (examiner) while the operation panel 108 is located in the same position as the position on the guide rail part 109 illustrated in FIG. 5B. In this state, the operator (examiner) visually recognizes the display on the display part with ease.

Figure 6:
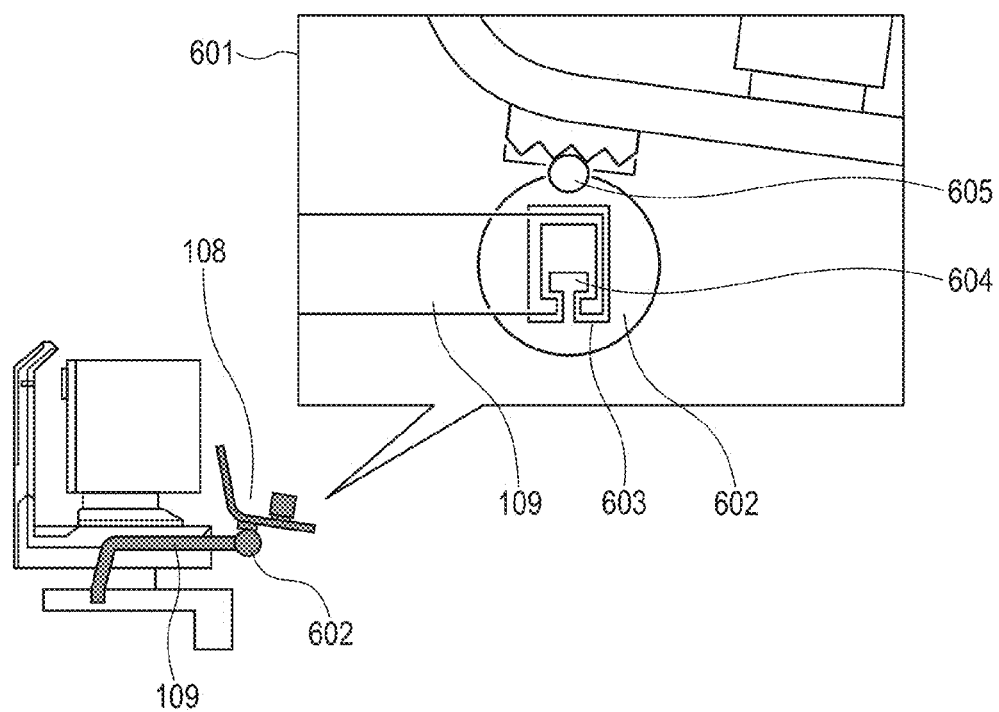
FIG. 6 is a diagram illustrating an example of a mechanism for mounting an operation panel on a guide rail part.

FIG. 6 is a diagram for illustrating an example of a mechanism for mounting the operation panel 108 on the guide rail part 109 slidably and rotatably in this embodiment.

FIG. 6 illustrates a mounting cross-section 601 of the guide rail part 109 and a mounting member 602. The guide rail part 109 is formed to be hollow (tubular), and is opened downward through a groove 603. The mounting member 602 annularly covers the guide rail part 109, and in addition, a screw 604 is inserted thereinto through the groove 603.

The screw 604 prevents the mounting member 602 from rotating about an axial center of the guide rail part 109, and also guides the mounting member 602 in moving along an extending direction of the guide rail part 109. The mounting member 602 and the operation panel 108 are connected to each other so as to be able to rotate by a shaft 605 within a horizontal plane. Note that, modes of the guide rail part 109, the mounting member 602, and the like are not limited to the above-mentioned forms. It suffices that the operation panel 108 is supported so as to be able to slide in the extending direction of the guide rail part 109, and it is further preferred that the operation panel 108 be supported so as to be able to rotate about an axis along a direction perpendicular to a sliding direction. Further, it is preferred that the guide rail part 109 be located around the rack part 107 in a state in which the frame part 103 is located substantially perpendicularly to the installation surface. However, an extending area thereof can be defined as an arbitrary range depending on such a sliding range of the operation panel 108 as to be requested when the eye is examined in actuality.

According to this embodiment, it is possible to realize the ophthalmologic apparatus that easily assists the examiner appropriately while easily achieving alignment between the operation direction of the operation member and the movable direction of the apparatus and thus facilitating the operator's operation. Further, by being combined with the configuration according to the first embodiment in which the elevation angle can be changed, it is possible to provide the examinee with an examination environment imposing a lower load.

(Third Embodiment)

As a third embodiment of the present invention, an example of an ophthalmologic apparatus including a light-emitting part extending over substantially the entire perimeter of the frame part 103 including the chin rest part 104 and the forehead rest 105 is described.

In FIG. 1B, the light-emitting part 111 is provided so as to surround the eyepiece part 106, the chin rest part 104, and the forehead rest 105 over substantially the entire perimeter of the frame part 103.

Such a light-emitting part can be realized by, for example, an optical fiber of a side surface light emitting type which is connected to the light source such as an LED.

In ophthalmologic observation, above all, the observation of a posterior eye segment, optical observation is performed through the eye of the examinee, and hence it is advantageous that a pupil thereof is dilated. Therefore, it is desired to keep an examination room dark before the observation. On the other hand, however, in order to perform the ophthalmologic observation, it is necessary to guide the examinee to the apparatus and ask the examinee to fix his/her face in a proper position by a chin rest part and a forehead rest. Therefore, in this embodiment, the light-emitting part 111 is provided in order to clearly indicate the position in which the examinee is to fix his/her face even in a darkroom. The light-emitting part 111 informs the examinee of the position of a frame part by emitting light.

Incidentally, when the light-emitting part 111 is formed of, for example, a point light source, it is not clear how the chin rest part and the forehead rest are located relative to the position of the light source. Further, most other interior light sources such as a lighting instrument and a power switch are also point light sources, and hence it is sometimes difficult to distinguish the light-emitting part 111 therefrom. Therefore, the light-emitting part 111 is provided so as to extend over substantially the entire perimeter of the frame part 103 including the chin rest part 104 and the forehead rest 105.

With this configuration, it is possible to guide the examinee as "Please fix your face within this circle of light". In other words, it is possible to realize the ophthalmologic apparatus in which the chin rest part 104 and the forehead rest 105 are so clear in position as to be preferred for fixing the face and are also easily distinguished from the interior other light sources.

When the chin of the examinee is put on the chin rest part 104 or when the forehead of the examinee is brought into abutment with the forehead rest 105, it is no longer necessary to present the position of the apparatus to the examinee. Therefore, when a sensor provided to the chin rest part 104 or the forehead rest 105 detects the placement of the chin or the abutment with the forehead, the light-emitting part 111 is slowly turned off so as not to surprise the examinee. The detection of the abutment or the like and the turning-off of the light-emitting part 111 are executed by a module area that functions as a light-emitting part control part in the system control part 222. Further, the system control part 222 may be configured to issue a control signal that turns on other illumination apparatus in order to allow the interior illumination to increase in brightness when the observation/photographing of the eye to be examined is finished.

According to this embodiment, it is possible to provide the ophthalmologic apparatus in which the chin rest part and the forehead rest are so clear in position as to be preferred for fixing the face while being easily distinguished from another light source even in a dark place. Further, by being combined with the configuration according to the first embodiment in which the elevation angle can be changed or the configuration according to the second embodiment which allows the movement of the operation panel, an examination environment imposing a lower load can be provided to the examinee.

As described above, according to the present invention, it is possible to provide the ophthalmologic observation/photographing apparatus with which an examination is easy to carry out even for an examinee such as a bent elderly person whose face is hardly fixed substantially perpendicularly.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-013588, filed Jan. 28, 2014, which is hereby incorporated by reference wherein in its entirety.

What is claimed is:

1. An ophthalmologic apparatus, which is configured to perform observation and photographing of an eye to be examined via an objective lens, the ophthalmologic apparatus comprising:
 a main body part comprising an optical system and the objective lens that are configured to perform the observation and the photographing;
 a stand part configured to support the main body part with respect to an installation surface;
 a chin rest part configured to place a chin of an examinee thereon; and
 a forehead rest configured to bring a forehead of the examinee into abutment therewith,
 wherein the chin rest part, the forehead rest, and the main body part are capable of integrally changing in elevation angle with respect to the stand part, while maintaining positional relationships of the chin rest part, the forehead rest, and the main body part.

2. An ophthalmologic apparatus according to claim 1, further comprising a grip handle part which is fixed to the main body part, configured to be grasped by the examinee while maintaining a posture at a time of the observation and the photographing of the eye to be examined,
 wherein the grip handle part, the chin rest part, the forehead rest, and the main body part are capable of integrally changing in the elevation angle with respect to the stand part, while maintaining positional relationships of the grip handle part, the chin rest part, the forehead rest, and the main body part.

3. An ophthalmologic apparatus according to claim 1, further comprising:
 a rack part supported by the stand part, configured to support the main body part slidably within a predetermined plane;
 a display part configured to display an image obtained by one of the observation and the photographing of the eye to be examined;
 an operation panel comprising an operation member configured to operate at least one operation portion of the display part and the main body part; and
 a guide rail part located around the rack part, and configured to support the operation panel slidably to move the operation panel around the main body part.

4. An ophthalmologic apparatus according to claim 3, wherein the guide rail part is configured to support the operation panel slidably and rotatably.

5. An ophthalmologic apparatus according to claim 1, further comprising:
 a frame part comprising the chin rest part and the forehead rest; and
 a light-emitting part which is provided on the frame part configured to inform the examinee of a position of the frame part by emitting light.

6. An ophthalmologic apparatus according to claim 5, further comprising a light-emitting part control part configured to sense one of a state in which the chin of the examinee is placed on the chin rest part and a state in which the forehead of the examinee is brought into abutment with the forehead rest, and turn off the light-emitting part in accordance with the sensing.

7. An ophthalmologic apparatus, which is configured to perform observation and photographing of an eye to be examined via an objective lens, the ophthalmologic apparatus comprising:
 a main body part comprising an optical system and the objective lens that are configured to perform the observation and the photographing;
 a stand part configured to support the main body part with respect to an installation surface;
 a display part configured to display an image obtained by one of the observation and the photographing of the eye to be examined;
 an operation panel comprising an operation member configured to operate at least one operation portion of the display part and the main body part; and
 a guide rail part located around the main body part, and configured to support the operation panel slidably to change a positional relationship between the main body part and the operation panel by moving the operation panel around the main body part.

8. An ophthalmologic apparatus according to claim 7, wherein the guide rail part is configured to support the operation panel slidably and rotatably.

9. An ophthalmologic apparatus, which is configured to perform observation and photographing of an eye to be examined via an objective lens, the ophthalmologic apparatus comprising:
   a main body part comprising an optical system and the objective lens that are configured to perform the observation and the photographing;
   a stand part configured to support the main body part with respect to an installation surface;
   a chin rest part configured to place a chin of an examinee thereon;
   a forehead rest configured to bring a forehead of the examinee into abutment therewith;
   a frame part comprising the chin rest part and the forehead rest; and
   a light-emitting part which is provided on the frame part, configured to inform the examinee of a position of the frame part by emitting light.

10. An ophthalmologic apparatus according to claim 9, further comprising a light-emitting part control part configured to sense one of a state in which the chin of the examinee is placed on the chin rest part and a state in which the forehead of the examinee is brought into abutment with the forehead rest, and turn off the light-emitting part in accordance with the sensing.

* * * * *